(12) United States Patent
Malin (10) Patent No.: US 6,478,524 B1
(45) Date of Patent: Nov. 12, 2002

(54) STORAGE ARRANGEMENT AND STORAGE RECEPTACLE WITH STORAGE ARRANGEMENT

(75) Inventor: Cosmas Malin, Nendeln (LI)

(73) Assignee: Liconic AG (LI)

(*) Notice: Subject to any disclaimer, the term of this patent is extended or adjusted under 35 U.S.C. 154(b) by 39 days.

(21) Appl. No.: 09/635,075

(22) Filed: Aug. 9, 2000

(30) Foreign Application Priority Data

Sep. 2, 1999 (CH) .............................................. 1601/99

(51) Int. Cl.$^7$ ................................................ B65G 1/06
(52) U.S. Cl. ........................ 414/283; 360/92; 414/277; 414/281
(58) Field of Search ................................. 414/277, 281, 414/282, 283, 217, 280, 286; 360/92

(56) References Cited

U.S. PATENT DOCUMENTS

| | | | |
|---|---|---|---|
| 3,302,804 A | * 2/1967 | Harris | ......................... 414/283 |
| 3,750,804 A | * 8/1973 | Lemelson | ............. 414/283 XL |
| 4,867,629 A | * 9/1989 | Iwasawa et al. | ........ 414/331.05 |
| 5,139,384 A | * 8/1992 | Tuttobene | ............. 414/277 XL |
| 5,143,193 A | * 9/1992 | Geraci | .................. 414/277 XL |
| 5,449,229 A | 9/1995 | Aschenbrenner et al. | |
| 5,733,024 A | 3/1998 | Slocum et al. | |
| 5,944,475 A | * 8/1999 | Bonora et al. | ......... 414/940 XL |
| 6,036,812 A | * 3/2000 | Williams et al. | ....... 414/283 XL |

FOREIGN PATENT DOCUMENTS

| | | | |
|---|---|---|---|
| DE | 200 04 202 | 8/2000 | |
| EP | 0 293 782 | 12/1988 | |
| EP | 0725 133 | 8/1996 | |
| JP | 405116708 | * 5/1993 | ................. 414/283 |
| WO | 98 05753 | 2/1998 | |
| WO | 99 15905 | 4/1999 | |

\* cited by examiner

Primary Examiner—Frank E. Werner
(74) Attorney, Agent, or Firm—Browdy and Neimark, P.L.L.C.

(57) ABSTRACT

The invention relates to a storage arrangement (15) and a storage receptacle (10) for objects (1), wherein the storage arrangement (15) has a storage device (14) with at least one storage shaft (14.1, 14.2) containing several storage spaces (13) arranged on top of each other, and a delivery device (34) for the short-term reception of the objects (1). The storage arrangement (15) furthermore has a transport device (16) with an object carrier (36), and has a vertical displacement device (40), a horizontal rotating device (38) and a horizontal displacement device (42) for displacing the object carrier (36) between the delivery device (34) and the storage spaces (13). The objects always take up the same angle in respect to the vertical line, wherein a base surface of the objects is preferably horizontally oriented. The storage receptacle (10) consists of a storage cabinet (12) and an integrated storage arrangement (15). The storage cabinet has a lock window opening, whose dimensions correspond to the dimensions of an object (1). The delivery device (34) is located outside the storage cabinet (12).

20 Claims, 4 Drawing Sheets

STORAGE ARRANGEMENT AND STORAGE RECEPTACLE WITH STORAGE ARRANGEMENT

FIELD OF THE INVENTION

The invention relates to a storage receptacle for objects, comprising a storage device and a transport device with an object carrier designed for respectively receiving an object. The invention furthermore relates to a storage receptacle comprising a storage cabinet for storing a plurality of objects and a storage arrangement which is designed integrally with the storage cabinet.

BACKGROUND OF THE INVENTION

Such a storage arrangement can be used by itself, i.e. without the storage cabinet, or integrally with the storage cabinet. The storage arrangement consists of a storage device and a transport device. The storage device contains storage spaces for storing objects, a transfer space for the short-term reception of objects prior to and following their storage, and a transport device for moving the objects between the delivery device and the storage spaces. The delivery spaces are formed by compartments, which are arranged on top of each other, of one or several storage shafts. The transport device is used for transporting the objects between the storage spaces and the delivery device, it comprises an object carrier, which is moved by means of a vertical displacement device, a horizontal rotating device and a horizontal displacement device.

A storage receptacle of the type mentioned essentially consists of a storage cabinet and a storage arrangement. The storage cabinet is designed in the manner of a housing and has a lock window opening in one of its walls, which can be closed by means of a lock window, through which objects can be passed prior to or after having been stored.

Within the framework of the present specification, objects are understood to be individual articles as well as containers with various contents, in particular also flowable contents.

A storage receptacle of the type mentioned at the outset is known from U.S. Pat. No. 5,449,229, for example. It is used for storing electronic storage devices, such as cassettes or CDs, and it could also be used in the same design for books, boxes and like objects. The delivery device of this storage receptacle is located in the interior of the storage cabinet, namely in its own cabinet section, and is designed for being able to receive a plurality of objects. The objects to be stored assume an oblique position in the storage cabinet, at the delivery device and during their transport by means of the transport device. In its dimensions the lock window opening corresponds to the delivery device in such a way that, with the lock window open, the entire delivery device is accessible from the exterior of the storage cabinet. Although this storage receptacle is suitable for its intended purpose, namely the storage of objects such as electronic storage devices, for which storage conditions, such as temperature, humidity and the type of the surrounding fluid need only be maintained within the widest margins, it is not suited for the storage of objects which need to be kept under controllable conditions or at least free of duct during a defined amount of time. The storage arrangement of this storage receptacle is unsuited to receive objects which are constituted by receptacles with contents of flowable materials and therefore must always assume a horizontal position.

Storage receptacles with controlled climatic conditions are needed, for example, if the objects to be stored are substances which are to be cultured and which optimally thrive only under defined temperature and humidity conditions, as well as in an exactly defined gasification atmosphere. Another application example for such storage receptacles is the short-term storage of substances Which must be stored while exactly defined climatic conditions are maintained. Since the substances to be processed are comparatively expensive, there is the desire to process them only in minimal amounts. Accordingly, correspondingly small storage devices, or respectively storage cabinets, are required for efficient processing or storage, while the requirements regarding the stability of the climate inside the storage cabinets nets rise out of proportion. Corresponding to the reduction of the storage devices and the storage cabinets, the permissible dimensions for the transport devices, which are used for loading and unloading the storage devices, also shrink, and the space requirement of each apparatus must be kept as small as possible.

As already mentioned, the storage receptacle in accordance with U.S. Pat. No. 5,449,229 is un-suitable for such purposes, namely in particular because of the design and arrangement of the delivery device and the dimensions of the lock window opening. The arrangement of the delivery device in the interior of the storage cabinet and its design for receiving a plurality of objects require that the lock window opening be comparatively large and that the lock window dow needs to be opened very often and/or for very long times, which is detrimental to the stability of the climate inside the storage cabinet.

A climate-controlled storage cabinet has become known from EP 0 293 782 which, however, also has a comparatively large opening for stocking and emptying. Since the dimensions of the opening are of importance for the stability of the climate which is all the greater, the smaller a climate-controlled cabinet is, no stable climatic conditions can be achieved in the interior of this climate-controlled cabinet because of the large opening.

Swiss Patent Application No. 1997 1097/97 describes a climate-controlled storage receptacle with a storage device in the form of a rotatable turntable. The transport device comprises a vertical displacement device, or respectively an elevator system for bringing an object carrier heightwise into a suitable position for the delivery of objects, and a horizontal displacement device for delivering or receiving objects. A horizontally-rotating device, by means of which the turntable is rotated, is used for the angular alignment of the object carrier on the storage device. Because of the space requirements for such a turntable, it is not possible to produce such a climate-controlled cabinet with an integrated turntable in a small size. Moreover, this arrangement is dynamically disadvantageous, since the comparatively large mass of the turntable must be accelerated and decelerated time and again.

U.S. Pat. No. 5,733,024 discloses a module-like system of a storage receptacle, and in particular a transport device in numerous variations, wherein practically all movement sequences which are possible at all are being described, which actually do not constitute an invention. But a storage receptacle with a single lock window opening is not described.

It can be stated that the previously known storage arrangements and storage receptacles do not meet the requirements which arise in the course of transporting and storing objects, and in particular in connection with processing of small amounts, but a large number, of substances. The problems in connection with the temporary storage of such substances under controllable climatic conditions in particular have not been resolved.

OBJECT AND SUMMARY OF THE INVENTION

It is therefore the object of the invention, to provide a storage receptacle of the type mentioned at the outset, which avoids the disadvantages of the prior art and permits an efficient manipulation of small objects, and to provide a storage receptacle of the type mentioned at the outset, which avoids the disadvantages of the prior art, wherein the exchange of the ambient air, or respectively ambient gas, occurring when the lock window is opened, is minimized.

In accordance with the invention, this object is attained in connection with the storage arrangement of the type mentioned at the outset by means of the features of the characterizing portion of claim 1, and in connection with a storage receptacle of the type mentioned at the outset by means of the features of the characterizing portion of claim 9.

Advantageous further developments of the storage arrangement of the invention and storage receptacle of the invention are respectively defined in dependent claims 2 to 8, or respectively 10 to 20.

The storage arrangement is designed in such a way that the transport paths and the masses, which must be accelerated, or respectively decelerated, in the course of transporting the objects, are small.

The objects can assume a horizontal, or at least approximately horizontal position in the storage spaces, in the delivery devices and on the object carrier. Therefore the storage arrangement is particularly, however not exclusively, suited for objects constituted by dishes or containers containing flowable masses, which therefore should no be tilted around horizontal axes.

The actual storage device comprises one or several storage shafts. Each storage shaft is designed in such a way that it has a compartment-like storage space respectively on several levels, in which it can receive one or possibly several objects.

In general the storage shafts are not connected with each other. They are arranged in a star shape, so to speak, to constitute the storage device in such a way that their vertical center planes intersect in a common vertical axis. The objects can be individually transported. To this end, the objects are taken individually out of the storage shafts. However, the objects can also be transported in groups. To this end, they are transported together with the storage shaft in which they are arranged. Thus, in this case the storage device is not only used for storage, but also as a transport shaft, or respectively transport cask, for the objects.

The transport device of the storage arrangement has an object carrier for the temporary reception of respectively one object during its transport and serves three purposes: firstly, the transport device displaces the objects vertically over the height of the storage device, secondly, the transport device pivots the objects horizontally between angular positions, wherein the object carrier is oriented either to the opening of a storage shaft or to the delivery device, and thirdly, the transport device pushes the object carrier between an inner, or respectively transport, position, which it assumes during the vertical displacement and the horizontal displacement of the objects, and an outer, or respectively delivery, position, in which the object carrier can receive or deliver an object, to which end it projects into a storage shaft, or into the area of the delivery space. All movements of the objects are therefore caused by the transport device, in contrast to some of the known storage arrangements, in which the objects are moved not by the transport device, but by the rotatably designed storage device. The novel storage device is advantageous in comparison to the known turntable-like storage devices, because the alternating acceleration and deceleration of the relatively large mass of the turntable is avoided. Furthermore, no imbalance is created in case of irregularly, or respectively not completely, loaded storage devices. Moreover, it is simpler to install and remove storage devices, which need not move during the operation of the climate-controlled cabinet, in or from the climate-controlled cabinet. Finally, it is also possible by means of the novel arrangement to place the storage shafts into holding devices designed in the same way inside a storage cabinet, in particular a climate-controlled cabinet, during the treatment of objects, and outside of the storage cabinet during the storage of objects.

In general, the storage spaces of the storage shafts, and the delivery device designed as a transfer platform do not have continuous deposit surfaces forming the receiving elements for the objects, but only lateral support strips extending in the direction of the respective linear displacement of the object carrier. Thus, objects located in the storage spaces, or respectively in the transfer device, only rest with their lateral edge zones on the support strips. The support plate used as an object carrier and which can have openings, is narrower as a whole than the mutual distance of the support strips of a compartment. Therefore objects resting on the object carrier only rest with a center zone on the object carrier. To pick up an object from the support space, the unloaded object carrier is brought underneath the object at the elevation of a lower limit of a level, is then raised to an upper limit of the same level, in the process of which it lifts the object off the support strips, and finally the object carrier is retracted out of the compartment at the upper limit. To place an object into a storage space, the process is reversed. In an analogous manner, and with a suitable design of the delivery device, an object can be taken from the delivery device by the object carrier, or respectively transferred to the delivery device by the object carrier. The just described arrangement makes it possible to avoid tilting the objects and to always store, or respectively transport, them in the same position in respect to the vertical direction.

At its outer edge facing away from the vertical axis of the transport device, and on its inner edge facing the vertical axis of the transport device, the object carrier can have positioning elements, which provide the correct positioning of the objects on the object carrier when picking up the objects and transporting them.

It has furthermore been shown to be advantageous to provide the object carrier with lateral guide elements in order to guide the objects when they are being received on the object carrier and to position them on the object carrier during their further transport, or respectively to prevent them from being laterally displaced in respect to the object carrier. It is particularly advantageous to mount the lateral guide elements in such a way that they perform the vertical displacement and the horizontal pivoting together with the object carrier, but do not perform the horizontal displacement. An object which is taken out of a storage space or a delivery device with the aid of the object carrier is being pulled during the horizontal movement of the object carrier from the outer transfer position into the inner transfer position between the lateral guide elements, which are fixed in place, so to speak.

For transferring the objects between the object carrier and one of the storage spaces or the delivery device, the objects and the object carrier can also be designed and operate in the manner of pallets and fork lifts. The object carrier of the transport device, which receives objects which are to be transported individually during the transport, can also be designed in a manner not represented as a gripper device for grasping and holding the objects.

The novel storage receptacle comprises the actual storage cabinet, as well as a storage arrangement, such as described above, arranged in the storage cabinet. The novel storage receptacle has at least one lock window opening, which is oriented toward the delivery device of the storage arrangement. In accordance with the invention, the dimensions of the lock window opening are only slightly larger than the dimensions of one of the objects. It is achieved by means of this that the climate in the storage cabinet is practically unaffected by the opening of the lock window, so that the stability of the climate is very great. Moreover, the delivery device is arranged outside of the storage cabinet, so that no space for it is needed anymore inside the actual storage area.

This novel storage receptacle is particularly suited for the storage and transportation of substances, or respectively objects, used in minimal amounts, because they are compactly constructed, so that the space requirements, as well as the transport distances, are minimized. Because of its great climatic stability, the novel receptacle is also advantageous for minimal amounts, since adverse climatic conditions have particularly grave results in connection with the processing of minimal amounts.

The delivery device in the storage cabinet is designed in such a way that it can preferably receive one, but also several objects awaiting further transportation.

If the objects contain flowable materials, it is advantageous, or even imperative, to always maintain them in the horizontal position, or respectively not to tilt them around a horizontal position. For this purpose the storage spaces and the delivery device are designed as horizontal lateral depositories, as described above, and the transport device is designed, as described above, in such a way that the objects are always in a horizontal position on the object carrier.

In addition to the lock window opening, the storage cabinet advantageously has a further opening, namely a door opening which is closed by means of a door. This is intended to constitute a transport path for at least one storage shaft of the storage device when the door is open, wherein the door opening in general is arranged on a wall different from the lock window opening. When being transported, the storage shafts, which are therefore used as transport shafts, or respectively transport casks, can be entirely or partially filled with objects, or they can be empty.

The storage cabinet can be climatized, or respectively designed as a climate-controlled cabinet. In this case the space it encloses is preferably divided into a climate-controlled zone, in which the storage device and the transport device are arranged, and an apparatus zone, in which a climate generator, and preferably the control for the transport device and/or the lock window, are arranged. For operating the climate-controlled cabinet it is generally advantageous to arrange the apparatus zone in the extension of the vertical axis, i.e. below or above the climate-controlled zone.

It is particularly advantageous for this if the storage shafts are separated from each other and can be individually removed from the climate-controlled cabinet.

In an advantageous embodiment, the storage device contains at least two storage shafts, which are arranged in a star shape around a vertical axis in such a way, that their vertical center planes intersect in the vertical axis, wherein the inlet, or respectively outlet, openings of the storage shafts are oriented toward the vertical axis constituting the pivot axis of the horizontal rotating device.

A device, which opens the lock window as soon as the elevation and angular position of the object carrier is aligned with the lock window for delivering or receiving an object, makes the operation of the climate-controlled receptacle efficient.

In certain cases it can be advantageous to protect the delivery device by providing it with a hood-like protecting device.

Further properties and advantages of the invention will be described in what follows by means of exemplary embodiments and by making reference to the drawings.

DETAILED DESCRIPTION OF THE PREFERRED EMBODIMENTS

Figure 1:
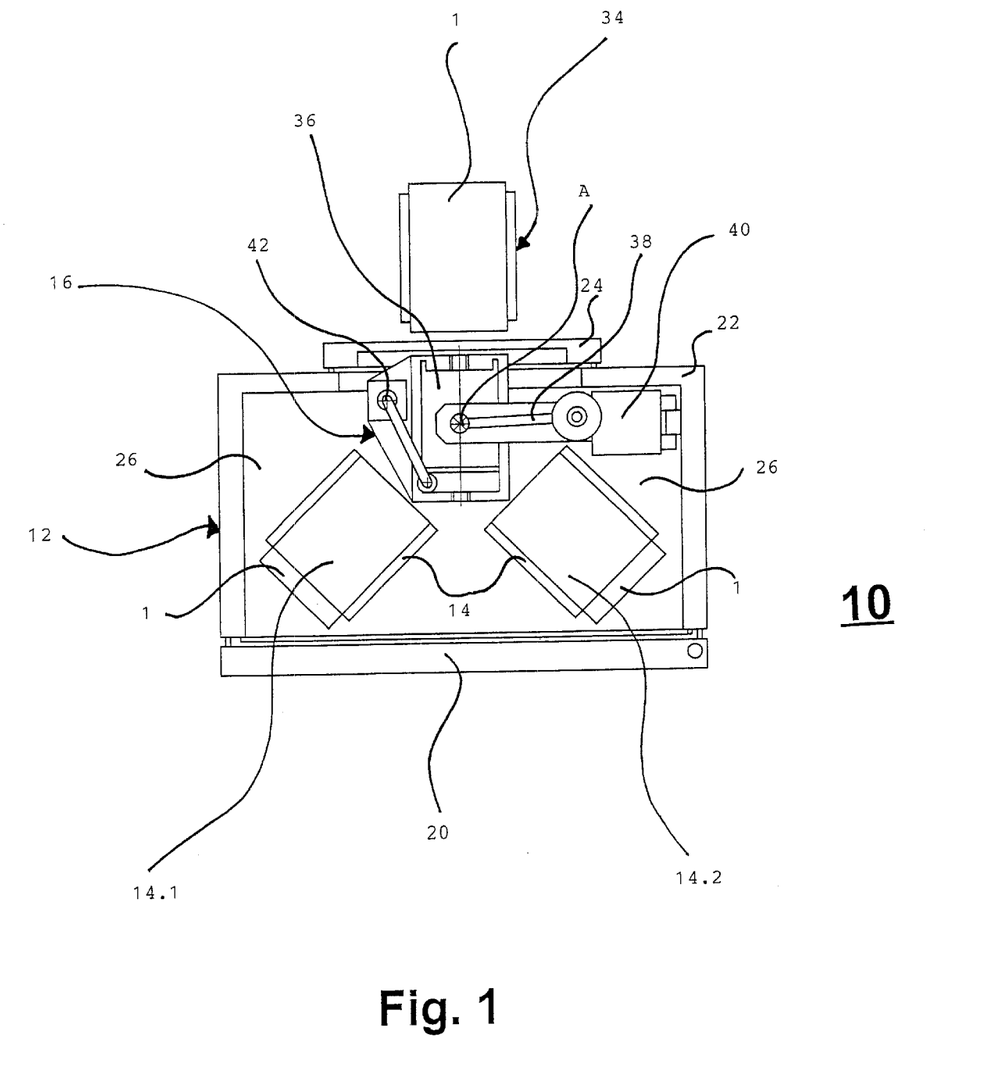
FIG. 1 is a view from above on a first exemplary embodiment of a climate-controlled receptacle in accordance with the invention, but without the ceiling which closes the climate-controlled cabinet at the top.
Figure 2:
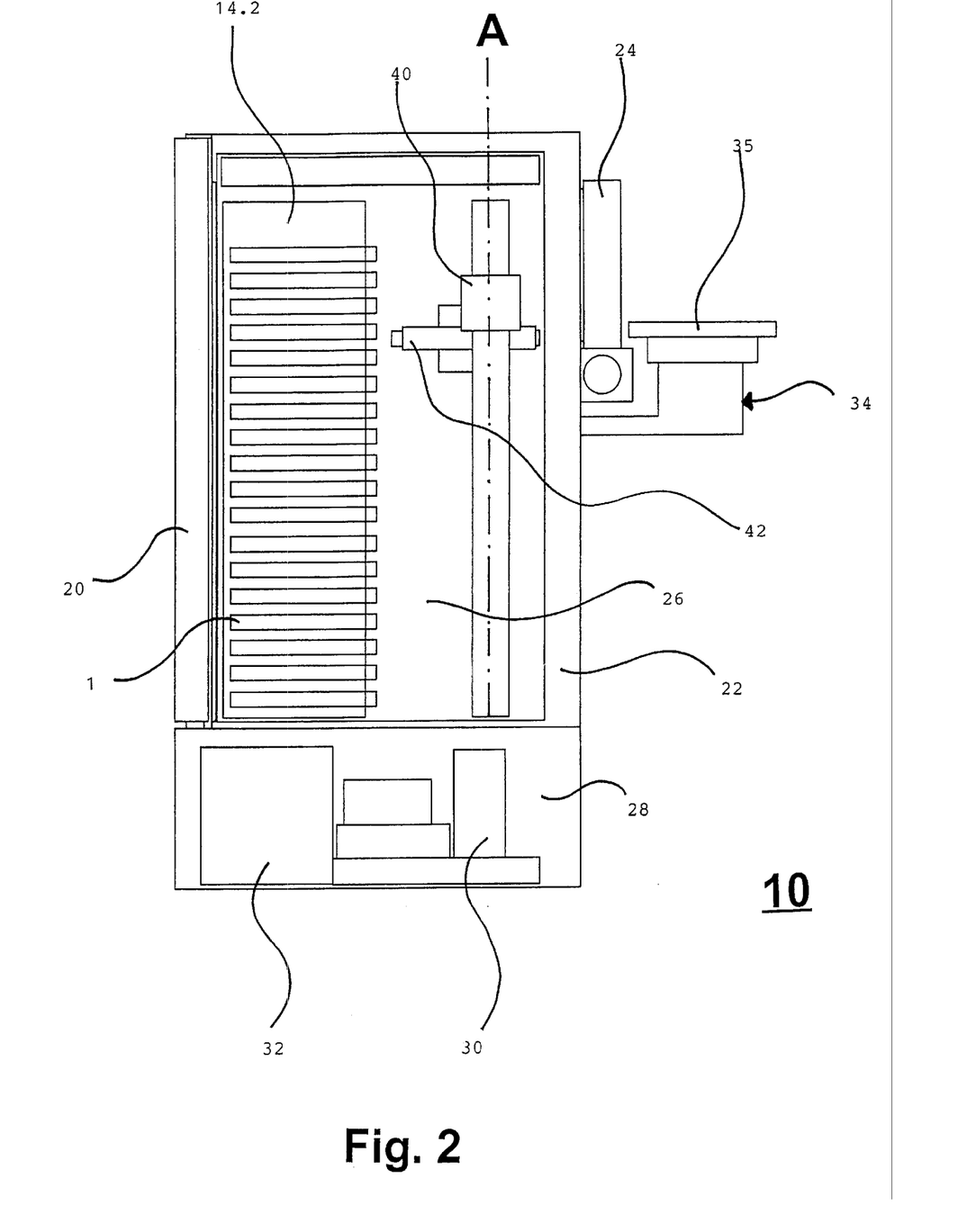
FIG. 2 is a lateral view of the climate-controlled receptacle represented in FIG. 1, but without the lateral wall facing the viewer.

The storage receptacle 10 represented in FIGS. 1 and 2 comprises an actual storage cabinet 12, a storage device 14 arranged in the storage cabinet 12, and a transport device 16, essentially arranged in the storage cabinet 12. Together, the storage device 14 and the transport device 16 constitute a storage arrangement 15. It should be noted in this connection, that such a storage arrangement could also be arranged and be operational outside of the climate-controlled cabinet 12.

In a first vertical wall 18, the storage cabinet 12 has a door opening provided with a door 20, and in a second vertical wall 22 it has a lock window opening provided with a lock window 24. The door opening 20 is used for moving the storage shafts 14.1, 14.2 in and out, as well as for cleaning and maintaining the interior of the storage cabinet 12. The door 20 can generally be manually operated. The lock window opening is used for introducing and removing individual objects 1 into, or respectively from, the interior of the storage cabinet 12 by means of the transport device 16. The opening and closing of the lock window 24 is automatically controlled. A device, not represented, is provided for this, by means of which the lock window 24 is automatically opened as soon as an object 1 is ready, or respectively arranged in respect to its elevation and angular position in such a way that it can be pushed through the lock window 24.

The interior of the storage cabinet 12 designed as a climate-controlled cabinet is divided into a climate-controlled zone 26 and an apparatus zone 28. The door 20 and the lock window 24 are arranged at the level of the climate-controlled zone 26. The storage device 14 with the objects 1 arranged in the storage shafts 14.1,14.2, as well as the essential components of the transport device 16, are located inside the climate-controlled zone 26. A climate generator 30, as well as a control device 32 for controlling the operation of the lock window 24 and the transport device 16, are located in the apparatus zone 28, which is arranged underneath the climate-controlled zone.

A delivery device 34 of the storage arrangement 15 is arranged outside of the storage cabinet 12 at the outside of the wall 22 and in front of the lock window opening. The delivery device 34 is designed in the form of a transfer platform 35 and has a horizontal effective surface. The effective surface is located at the level of the lower edge of the lock window opening of the lock window 24 and is intended for the short-term reception of one of the objects 1, this respectively prior to the reception or after the delivery of this object 1 from, or respectively to, an object carrier 36 of the transport device 16, or from, or respectively to, an external transfer device, not represented. The object carrier is essentially designed in the shape of a plate and can also be called a carrier plate.

In the present case the storage device 14 comprises two storage shafts 14.1, 14.2, which are separate from each other and are fixedly mounted inside the climate-controlled cabinet 12, i.e. they cannot be rotated, such as was the case with turntable-like storage devices of previously known climate-controlled storage cabinets. A plurality of compartment-like storage spaces 13 is arranged on top of each other in each one of the storage shafts 14.1, 14.2. These storage spaces 13 are provided for receiving the objects 1, wherein generally, but not absolutely necessarily, one object 1 is received in each one of the compartments.

The transport device 16 has the carrier plate constituting the object carrier 36, which is designed for receiving respectively one object 1. The transport device 16 has the vertical axis A, which coincides with the intersection line of the vertical plane of symmetry of the storage shafts 14.1,14.2, which are arranged in a star shape around the vertical axis A.

The transport device 16 has a horizontal rotating device 38, by means of which the object carrier 36 can be pivoted around the vertical axis A and brought into an angular position, in which the object carrier 36 is aligned with one of the storage shafts 14.1,14.2, or respectively with the respective openings, or with the lock window 24, or respectively the delivery device 34.

The transport device 16 furthermore has a vertical displacement device 40, or respectively an elevator, for displacing the object carrier 36 in the vertical direction and to bring it to defined levels in the process. The arrangement in regard to the levels, and the vertical distance between the levels, correspond to the storage spaces 13. Basically, it is necessary to bring the object carrier 36 to one of the defined levels in order to deliver one of the objects 1 to a the storage space 13 or to the delivery device 34, or respectively to receive it from a storage space 13 or from the delivery device 34. Each one of the defined levels preferably extends over a small vertical distance between an upper and a lower limit. In this case the vertical distance between the lower and upper limit of a level is much less than the vertical distance between adjoining levels. The purpose of this arrangement will be explained further down below.

Finally, the transport device 16 has a horizontal displacement device 42. The object carrier 36 can be linearly displaced by means of this horizontal displacement device 42 between an inner, or respectively transport, position, represented in FIG. 1, and an outer, or respectively delivery, position. The displacement of the object carrier 36 between the inner, or respectively transport, position, and the outer, or respectively delivery, position takes place at several occasions, namely always at the time when the object carrier 36 delivers one of the objects 1 to one of the storage spaces 13, or through the lock window 24 to the delivery device 34, and of course also when the object carrier 36 picks up one of the objects 1 from one of the storage spaces 13 or from the delivery device 34.

Various suitable conventional drive mechanisms can be used for driving the horizontal rotating device 38, the vertical displacement device 40 and the horizontal displacement device 42, for example by means of belts or toothed racks and pinion gears, or also by means of a fluid activation.

Generally the storage spaces 13 of the storage shafts 14.1, 14.2 and the transfer platform 35 of the delivery device 34 do not have continuous deposit surfaces constituting the receiving elements for the objects 1, but only lateral support strips extending in the direction of the respective linear displacement of the object carrier 36. Thus, objects 1 located in the spaces 13, or respectively the delivery device 34, only rest with their lateral edge areas on the support strips. The carrier plate used as the object carrier 36, which can have openings, as a whole is narrower than the mutual distance of the support strips of a compartment. Therefore objects 1 resting on the object carrier 36 only lie with a center area on the object carrier 36. To pick up an object 1 from a storage space 13, the empty object carrier 36 is brought underneath the object 1 at the elevation of the lower limit of a level, is then raised to the upper limit and in the process lifts the object 1 off the support strips, and finally the object carrier 36 is pulled back out of the compartment at the elevation of the upper limit. The reverse process takes place for taking an object 1 into the storage space 13. In an analogous manner, and with a suitable design of the delivery device 34, an object 1 can be transferred from the delivery device 34 by the object carrier 36, or respectively can be delivered to the delivery device 34 by the object carrier 36. The just described arrangement makes it possible that the objects 1 are not tilted, but are always stored, or respectively transported, in the same position in respect to the vertical.

Figure 4A:
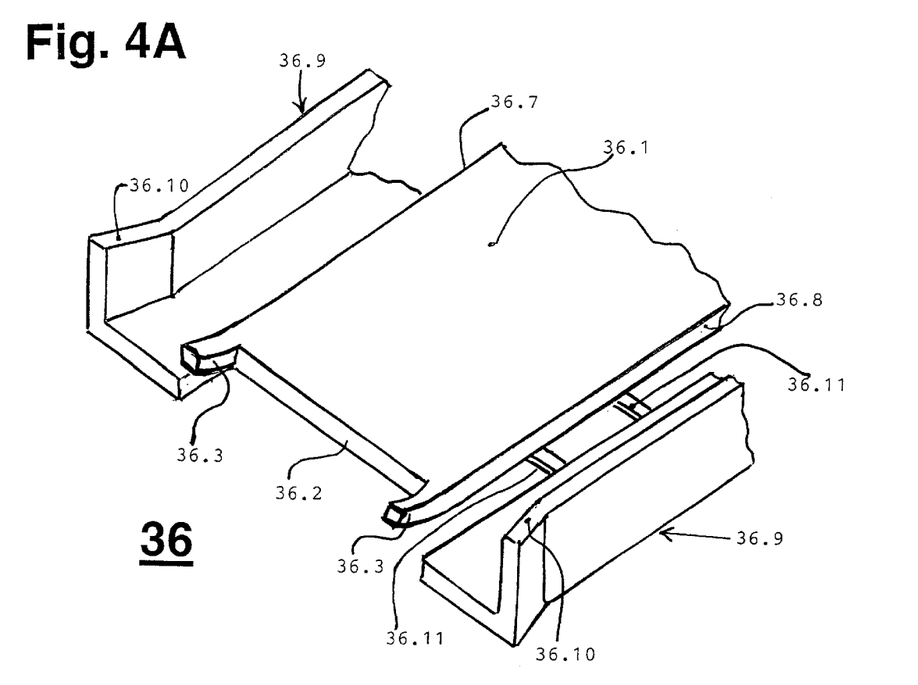
FIG. 4A is diagram of an exemplary embodiment of an object carrier.
Figure 4B:
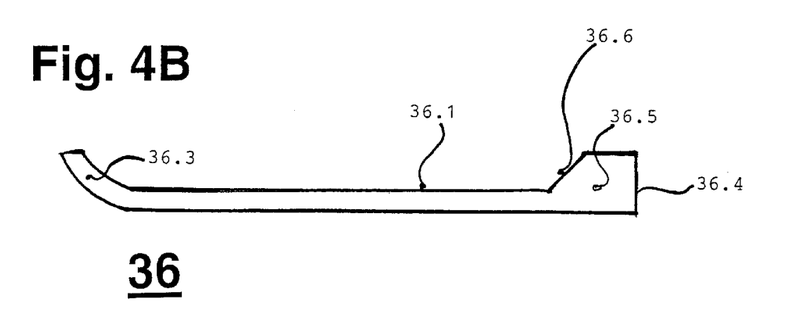
FIG. 4B shows the object carrier represented in FIG. 4A in vertical section.

FIGS. 4A and FIG. 4B show an object carrier 36. An actual support surface 36.1 is used for respectively one of the objects 1. The support surface 36.1 has positioning elements 36.3 on its edge 36.2 extending transversely to the horizontal displacement of the object carrier 36. This edge 36.2 constitutes the outer limit of the object carrier 36 and is in front, when the object carrier 36 is pushed into a storage place 13 or into the delivery device 34. The positioning elements 36.3 are constituted by lateral protrusions, which extend upward transversely to the support surface 36.1. They provide that the object carrier 36 actually takes along an object 1 removed from a storage space 13 or the delivery device 34. A further positioning element 36.5 is arranged on the edge 36.4 of the object carrier 36 which lies opposite the edge 36.1. It is constituted by an edge strip, which extends upward transversely in respect to the support surface 36.1 and has an inclined surface 36.6, which falls away toward the support surface 36.1. An object 1, which inadvertently comes to rest too close to the edge 36.3 of the object carrier 36, and therefore is canted, slides along the inclined surface 36.6 onto the support surface 36.1 into a horizontal position. The positioning elements 36.3 and 36.5 can also be designed differently in their details.

Furthermore, lateral guide elements 36.9 are provided for guiding, or respectively positioning, the objects 1, which are oriented parallel with the lateral edges 36.7, 36.8 of the object carrier 36. These lateral guide elements 36.9 are not mounted fixed on the support surface 36.1 of the object carrier 36, but are fastened in such a way that they are moved together with the object carrier 36 by means of the horizontal rotating device 38 and the vertical displacement device 40, but do not participate in the movement of the object carrier 36 through the horizontal displacement device 42. When being picked up, an object 1 is pulled, so to speak, between the lateral guides 36.9 in the course of the horizontal movement of the object carrier 36. Here, pre-positioning by means of the inclined walls 36.10 of the lateral guide elements 36.9 can take place. The lateral guide elements 36.9 have a cross section which has at least approximately the shape of a letter L. They are fastened by means of strips 36.11, and their mutual distance from each other, or respectively their distance from the support surface 36.1 can be adjustable. By way of example, FIG. 4B shows the two edge strips 36.9 in different positions, wherein the lateral guide element 36.9 extending along the edge 36.8 is farther removed from the support surface 36.1 than the lateral guide element 36.9 extending along the edge 36.7.

For transferring objects 1 between the object carrier 36 and one of the storage spaces 13 or the delivery device 34, the undersides of the objects 1 and of the object carriers 36 can also be designed and act in the manner of pallets, or respectively forks of a forklift. Moreover, the transfer of the objects 1, in particular between the object carrier 36 and the delivery device 34, can also be performed with the aid of pushers or tong-like elements, in particular, if tilting of the object can be tolerated. In this case it is not necessary to provide two limits for each level.

Figure 3:
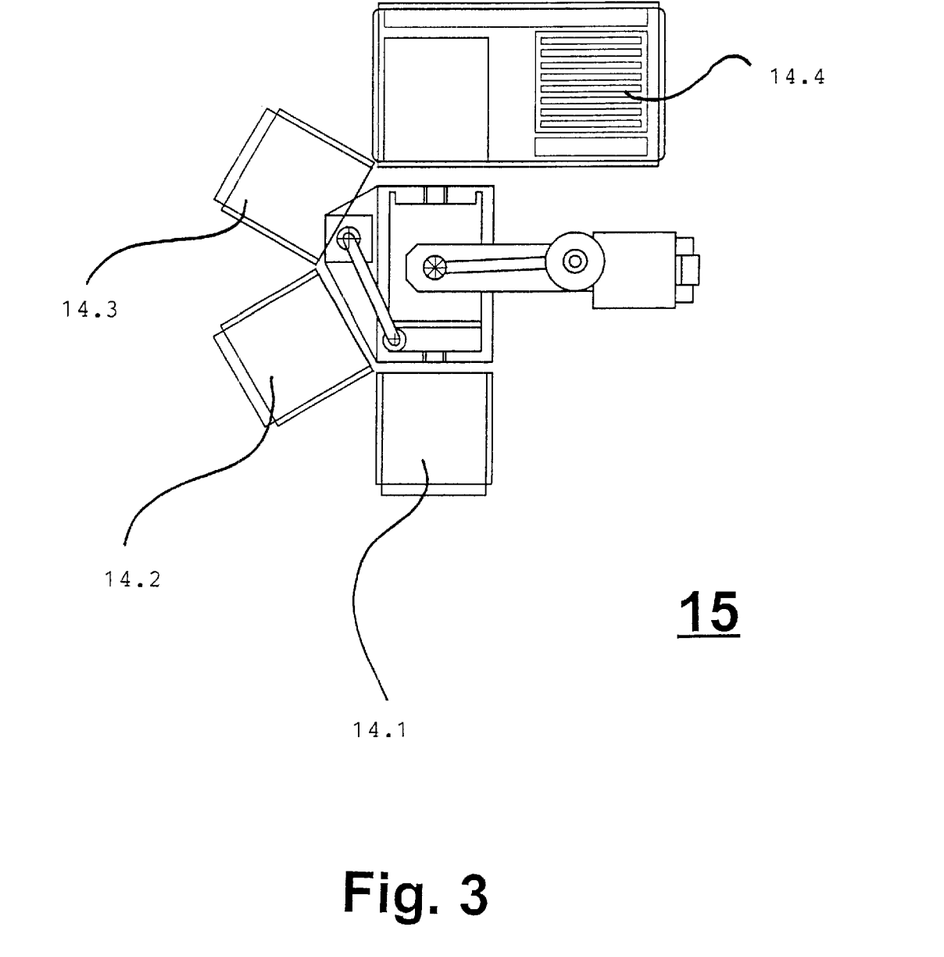
FIG. 3 is a view from above on a second exemplary embodiment of a climate-controlled receptacle in accordance with the invention in a simplified representation.

In connection with the storage receptacle 10 represented in FIGS. 1 and 2, a storage device 14 with only two storage shafts 14.1, 14.2, which can also be used as transport casks, has been installed. Within the scope of the invention, or respectively in accordance with FIG. 3, it is also possible to design storage devices 14 with more than two storage shafts, or respectively transport units, which are all arranged in a star shape around the axis A. The number of storage shafts which can be arranged is a function of the proportions in size. Each one of the storage shafts requires approximately one shaft sector of a fictitious cylinder with the vertical axis A. A sector intended for the lock window 24 and the transport device 16 may not be occupied by a storage shaft, wherein this sector possibly extends over a larger angle than the shaft sectors. The storage shafts, or respectively storage units, or a storage device need not all be designed the same. FIG. 3 represents a storage arrangement 15 with a storage unit 14.4 in the form of a reader, or respectively dispenser, and three storage shafts 14.1, 14.2, 14.3 with cassettes.

The storage receptacle can also be designed in such a way that, in addition to the said lock window opening, the storage cabinet has a further lock window opening. With such an arrangement it is possible to use respectively one of the lock window openings for delivering and removing the objects.

Alternatively, the storage receptacle can also be designed in such a way that a lock window opening is located in an upper horizontal covering, i.e. in the lid, or lower horizontal covering, i.e. in the bottom, or that it has two lock windows, respectively one in the lid and in the bottom. Then the objects are delivered, or respectively removed, in the vertical direction. Such an arrangement permits a completely star-shaped arrangement of the storage shafts covering 360.

As mentioned above, FIGS. 1, 2 and 3 represent a storage receptacle 10 with the storage cabinet 12 and the storage arrangement 15 arranged therein, which consists of the storage device 14 and the transport device 16. As already mentioned, the same storage arrangement can also be used outside of a storage cabinet in a manner not represented.

What is claimed is:

1. A climate controlled cabinet for storing a plurality of objects comprising:
    a front wall and a back wall,
    a climate generator,
    at least one lock window opening closed by means of a lock window in said back wall of the cabinet, and a storage arrangement for storing and handling the objects in the cabinet, said storage arrangement comprising:
        a) a storage device with
            a1) exactly two storage shafts non-rotationally mounted inside the climate controlled cabinet, wherein each storage shaft comprises:
            a11) several storage spaces arranged on top of each other for receiving an object each,
            a12) a vertical center plane and
            a12) an opening for inlet and outlet, wherein said storage shafts are arranged around a vertical axis in such a way that their vertical center planes intersect in the vertical axis, and wherein the openings for inlet and outlet of the storage shafts are facing the vertical axis, and
        a2) a delivery device comprising a transfer platform arranged outside the cabinet in an area of the lock window opening for temporarily receiving the objects prior to or after storage, and
    b) a transport device positioned between said lock window and said storage shafts, said transport device having an object carrier and said object carrier comprising a carrier plate having a support surface for receiving one object, which transport device has
        b1) a vertical displacement device for displacing the object carrier along said vertical axis over the height of the storage device and for bringing the object carrier to a transfer level for each of the storage spaces or for the delivery device,
        b2) a horizontal rotating device for pivoting the object carrier around said vertical axis and for aligning it with one of the storage spaces or the delivery device, and
        b3) a horizontal displacement device for displacing the object carrier between an inner transport position, where the object carrier is vertically displaceable and horizontally pivotal, and an outer transport position, where the object carrier is arranged during a transfer of the objects between the object carrier and one of the storage spaces or the delivery device, wherein said storage shafts are arranged in opposite halves of said cabinet.

2. The climate controlled cabinet of claim 1 wherein the objects are arranged horizontally in said storage spaces, on said delivery device and on said object carrier.

3. The climate controlled cabinet of claim 1 wherein said delivery device is designed for receiving a single one of said objects.

4. The climate controlled cabinet of claim 1 wherein said support surface has an outer edge and an inner edge transversely oriented in respect to a horizontal displacement direction of the object carrier, and wherein said object carrier comprises
    first upwardly extending positioning elements at said outer edge, and a second upwardly extending positioning element at said inner edge.

5. The climate controlled cabinet of claim 4 wherein said first upwardly extending positioning elements comprise two lateral protrusions.

6. The climate controlled cabinet of claim 4 wherein said second upwardly extending positioning element comprises an inclined surface falling away towards said support surface.

7. The climate controlled cabinet of claim 1 comprising lateral guide elements arranged on the object carrier for guiding and positioning the objects, said lateral guide elements extending parallel to a horizontal displacement direction of the object carrier, wherein said guide elements are arranged at a constant distance from said vertical axis to follow said object carrier during movements generated by said vertical displacement device and said horizontal rotating device.

8. The climate controlled cabinet of claim 1 comprising a door opening closed by a door for forming a transport path for said storage shafts when said door is open.

9. The climate controlled cabinet of claim 1 wherein said cabinet is divided into a climate-controlled zone, where said storage device and said transport device are arranged, and into an apparatus zone comprising a climate generator and/or controls for said transport device or said lock window, wherein said apparatus zone is arranged above or below said climate-controlled zone.

10. The climate controlled cabinet of claim 1 wherein said storage shafts are separate from each other.

11. The climate controlled cabinet of claim 1 further comprising an opening device for opening said lock window when the object carrier is oriented towards said lock window in respect to its elevation and angular position for delivering or receiving an object.

12. The climate controlled cabinet of claim 1 wherein said delivery device is mounted to an outside of said back wall of said cabinet.

13. The climate controlled cabinet of claim 1 wherein said storage shafts are arranged at opposite angles in respect to said back wall.

14. The climate controlled cabinet of claim 1 comprising a door opening arranged opposite to said lock window and closed by a door for forming a transport path for said storage shafts when said door is open, wherein said halves are separated by a plane extending perpendicular to said door and said lock window.

15. The climate controlled cabinet of claim 1 wherein the dimensions of the lock window opening correspond to those of an object.

16. A climate controlled cabinet for storing a plurality of objects comprising:
   a front wall and a back wall,
   a climate generator,
   exactly storage shafts non-rotationally mounted inside the cabinet, wherein each storage shaft comprises
      several storage spaces arranged on top of each other for receiving an object each
      a vertical center plane and
      an opening for inlet and outlet,
   wherein said storage shafts are arranged around a vertical axis in such a way that their vertical center planes intersect in the vertical axis, and wherein the openings for inlet and outlet of the storage shafts are facing the vertical axis,
   a lock window opening closed by means of a lock window in said back wall,
   a door in said front wall for forming a transport path for said storage shafts when said door is open,
   a delivery device comprising a transfer platform arranged outside the cabinet at said lock window opening for temporarily receiving the objects prior to or after storage, and
   a transport device with an object carrier comprising a carrier plate having a supporting surface for receiving one object, which transport device has
      a) a vertical displacement device for displacing the object carrier along said vertical axis over the height of said storage shafts and for bringing the object carrier to a transfer level for each of the storage spaces or the delivery device,
      b) a horizontal rotating device for pivoting the object carrier around said vertical axis and for aligning it with one of the storage spaces or the delivery device, and
      c) a horizontal displacement device for displacing the object carrier between an inner transport position, where the object carrier is vertically displaceable and horizontally pivotal, and an outer transport position, where the object carrier is arranged during a transfer of the objects between the object carrier and one of the storage spaces or the delivery device, and
   wherein said storage shafts are arranged symmetrically with respect to a plane of symmetry, and said plane of symmetry intersects said front and back walls and extends through said door, said vertical axis, said lock window and said delivery device.

17. The cabinet of claim 16 wherein said plane of symmetry is perpendicular to said front and back walls.

18. The climate controlled cabinet of claim 16 wherein said transport device is arranged between said lock window and said storage shafts.

19. The climate controlled cabinet of claim 16 wherein said vertical axis extends through said object carrier in said inner transport position.

20. The climate controlled cabinet of claim 16 wherein said vertical axis is located between said lock window and said door.

* * * * *